United States Patent [19]
Thompson

[11] Patent Number: 4,649,909
[45] Date of Patent: Mar. 17, 1987

[54] COMPOSITE SURGICAL DRESSING

[75] Inventor: Darrell R. Thompson, Somerville, N.J.

[73] Assignee: Johnson & Johnson Products, Inc., New Brunswick, N.J.

[21] Appl. No.: 329,973

[22] Filed: Dec. 11, 1981

[51] Int. Cl.4 .............................................. A61L 15/00
[52] U.S. Cl. .................................... 128/156; 128/155
[58] Field of Search .................. 128/156, 155; 428/355

[56] References Cited
U.S. PATENT DOCUMENTS 3,645,835  2/1972  Hodgson .............................. 428/355
4,231,357  11/1980  Hessner ................................ 128/156

OTHER PUBLICATIONS

Brady, et al., "Comparison of Donor Site Dressings", Annal of Plastic Surgery, vol. 5, No. 3, Sep. 1980, pp. 238-243.

Primary Examiner—C. Fred Rosenbaum
Assistant Examiner—Sherri E. Vinyard
Attorney, Agent, or Firm—Michael Q. Tatlow

[57] ABSTRACT

A surgical dressing is disclosed which is composed of a polymeric film having a moisture vapor transmission rate between 15 and 80 grams per 100 sq. inches per 24 hours. There is an adhesive around the periphery on the lower surface of the film and a series of apertures through the film of the adhesive. There is an absorbent pad on the upper surface of the film secured in place by a fibrous covering material. The fibrous covering material is adhesively coated and is of the same dimensions as the film so that it may be removed without lifting the film from the skin of the patient.

5 Claims, 3 Drawing Figures

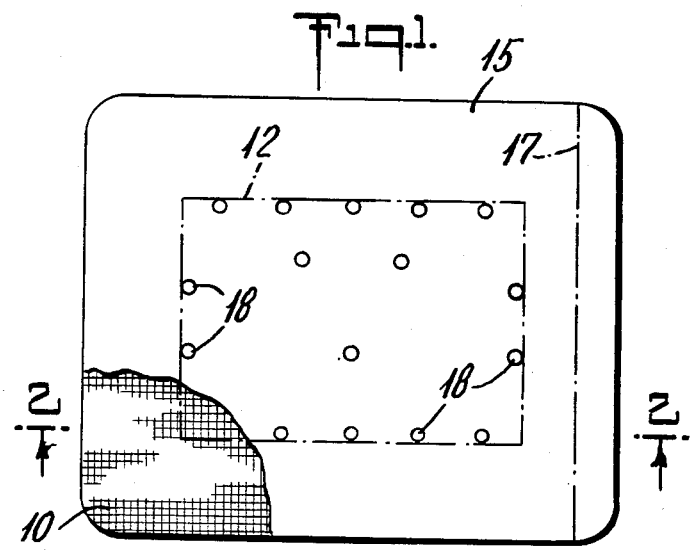
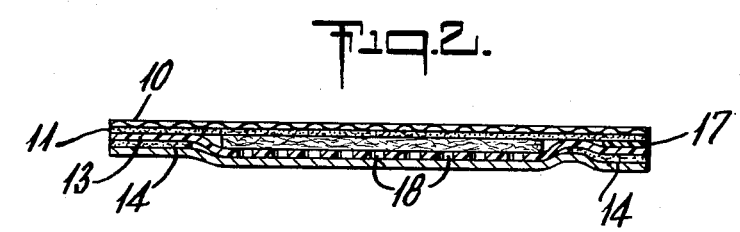
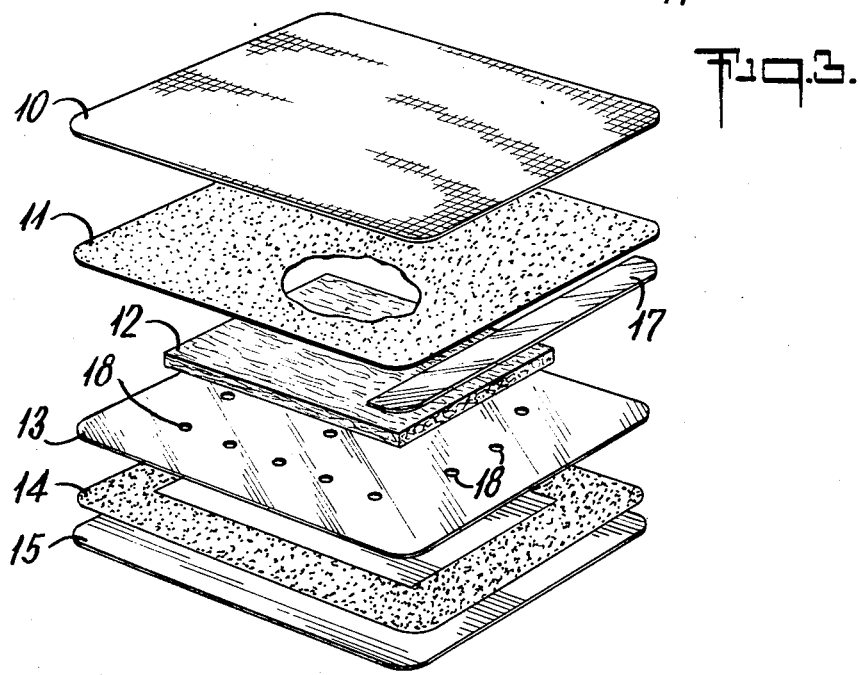

COMPOSITE SURGICAL DRESSING

FIELD OF THE INVENTION

This invention relates to surgical dressings of the type that are employed for relatively large surface area wounds such as skin graft donor sites, skin grafts and small burn dressings and other wounds which have significant amounts of wound exudate.

BACKGROUND OF THE INVENTION

Large area wounds, such as those made on a donor for a skin graft or the wounds to which the skin graft is applied on the patient and small second-degree burn wounds, present considerable problems in the application of surgical dressings to such wounds. These wounds must be protected against bacterial infection and yet they have a tendency to secrete or exude significant amounts of body fluids which must be removed from the wound site. Frequent changes of dressings on such wounds tend to interfere with the healing of the wounds, and such frequent changes may also increase the possibility that the wound can be contaminated by bacteria transmitted from the nurse or other specialist who is changing the dressing.

These wounds will also heal more rapidly if the wound is maintained under the proper conditions of relative humidity and is kept free of wound exudate.

Attempts to construct wound dressings for the control of the wound exudate and to balance the environmental condition of the wound are numerous. Examples of such dressings are those shown in U.S. Pat. Nos. 4,181,127; 4,231,357; 3,870,041; 3,888,247 and 3,521,631. Although the dressings shown in these references offer some advantages, they have not been totally successful in managing the large area wounds of the type that are discussed above.

SUMMARY OF THE INVENTION

The present invention provides a wound dressing which offers significant advantages in the control of infection, allows wound exudate to be removed without disturbing the surface of the wound and which offers significant advantages in controlling the environment of the wound surface. The dressing is made of two components. There is a primary dressing which is in contact with the skin and which may remain on the surface of the skin over an extended period of time, and in some instances until the wound is healed, to the extent that it no longer requires a surgical dressing. The dressing also has a secondary dressing component containing an absorbent material which will absorb wound exudates and which can be changed without disturbing the position of the primary dressing on the surface of the skin. The primary wound dressing of the composite dressing of this invention comprises a film which is very thin and can be readily contoured to fit the contours of the human body. This film has a moisture vapor transmission rate which is at least that of intact human skin. The film is attached around the wound area on intact skin by an adhesive which is applied to the periphery of the film. The secondary dressing is applied over the primary dressing and can communicate with the wound through perforations around the interior periphery of the adhesive coating on the film. The moisture vapor transmission characteristics of the film portion of the dressing prevent wound masceration by allowing moisture vapor to escape from the skin surface but allow oxygen to penetrate the film to aid in the wound healing process. Any wound exudate that may collect under the primary dressing is removed from the wound area through the perforations in the film and into the absorbent component of the dressing. The absorbent component of the dressing is maintained in position over the primary dressing by an adhesively coated fibrous backing which can be readily removed from the primary film dressing and replaced with a fresh absorbent dressing without disturbing the position of the film on the skin.

Since the film portion of the dressing can be maintained in its position on the skin over extended periods of time without fear of causing masceration, the wound healing process is not disturbed by the removal and changing of the secondary dressing.

DETAILED DESCRIPTION OF THE INVENTION

The invention will be better understood with reference to the drawings in which:

FIG. 1 is a top view of the dressing, partially broken away.

FIG. 2 is a side view of the dressing taken along lines 2—2 of FIG. 1; and

FIG. 3 is an exploded view of the dressing showing the various components and their relative position in the dressing.

The primary component of the dressing is a very thin, i.e., 0.5 to 5 mils, film which is shown as element 13 in the drawing. This film has a controlled moisture vapor transmission rate which is equal to or greater than that of intact human skin. The moisture vapor transmission rate is generally between 15 and 80 grams per 100 sq. inches per 24 hours as tested according to ASTM Test E96 at 100° F. and 90% relative humidity. This moisture vapor transmission rate allows the moisture vapor that is released from the skin to escape through the dressing, thereby avoiding the possibility of causing an accumulation of moisture and the resulting masceration of the skin beneath the primary dressing component 13. The primary dressing component 13 is secured to the skin of the patient by an adhesive coating 14 which is applied to the film 13 around the periphery of the film. The width of the adhesive is approximately ⅜ inch to ¾ inch. The preferred dressing to be used for a particular wound would be one which is of sufficient size so that the adhesive coating around the periphery of the primary dressing would not come into contact with the wound on the surface of the patient's skin. In addition to applying the adhesive around the periphery of the primary film dressing for manufacturing convenience, it is also possible to apply the adhesive over the entire film component of the dressing and overlay the adhesive with an additional film in the central position to prevent the adhesive coating from coming into direct contact with the wound of the patient.

There are a number of apertures 18 in the film portion of the dressing to allow wound exudate to be readily removed from the wound site. The size and number of apertures in the film must be selected to provide sufficient removal of the wound exudate and yet maintain the moisture vapor transmission characteristics of the major surface area of the film. As shown in the drawings, the preferred shape of the apertures is circular. Other shapes may also be employed, and the film apertures may also be provided by slitting the film. These apertures are primarily placed around the periphery of that portion of the dressing where the adhesive coating meets the area which is uncoated by adhesive. The apertures are approximately 1 to 2 millimeters in diameter and are spaced around the periphery 1 to 5 centimeters apart. There may be a small number of additional apertures through the center area of the dressing. The presence of apertures allows the wound exudate to be removed from the wound surface without puddling of the wound exudate on the wound surface.

The presence of the apertures does not materially alter the moisture vapor characteristics of the film in contact with the skin. In order for the moisture vapor to reach an aperture from the center of the dressing, it must diffuse laterally through the space between the skin and the film to the aperture. It has been found that lateral diffusion does not occur in any measurable quantity.

There is a pad of absorbent material 12 which is composed of absorbent fibers such as cotton, rayon or mixtures of cotton or rayon with woodpulp or mixtures of such absorbent fibers with a synthetic fiber such as polyester or polypropylene fibers. The absorbent pad is of a size to overlie the central area and the apertures in the primary dressing. The surface of the absorbent which is in contact with the apertures may be a non-adhering surface so the wound exudate will not directly adhere to the absorbent fibers of the dressing. Examples of such absorbent pads with non-adhering surfaces are disclosed in U.S. Pat. Nos. 3,434,472; 3,528,417 and 3,703,897.

There is a fabric backing 10 which is coated overall with an adhesive 11 which secures the absorbent pad 12 in its proper position over the primary film dressing component. The secondary dressing component is considered to be the absorbent pad 12 and the adhesive-coated fibrous backing 10. The fibrous backing may be any woven or nonwoven fabric or it may be a flexible paper material. The preferred fibrous backing is a warp knitted, cellulose acetate fiber material having a weight of approximately 2.3 ounces per square yard.

In order to allow the fibrous backing to be readily removed from the primary dressing, there is a non-adhering tab 17 which is positioned between the adhesive coating 11 and the top surface of the film 13. This tab allows the secondary dressing, made up of components 12 and 10, to be readily lifted from the primary dressing 13 without disturbing the position of the primary dressing on the skin of the patient. In order to insure that the position of the primary dressing is not disturbed on the patient's skin, it is important that the fibrous backing 10 be no larger in area than the area of the film component 13 of the primary dressing. If the adhesive contact area between the secondary component of the dressing is larger than the film or primary component of the dressing, the primary dressing is very often inadvertently lifted from the skin of the patient when the secondary dressing is removed.

The use of the secondary dressing allows the wound exudate to be readily removed with the absorbent pad 12 and a new secondary dressing can be readily positioned over the primary dressing without disturbing the position of the primary dressing on the patient's skin.

The use of a fibrous backing which is substantially opaque offers the additional advantage that it blocks the patient's view of the wound.

I claim:

1. A surgical dressing comprising:
   a polymeric film between 0.5 and 5 mils in thickness, the moisture vapor transmission rate of the intact film being between 15 and 80 grams per 100 sq. inches per 24 hours, said film having a top surface and a bottom surface,
   a skin adhering adhesive around the periphery of the bottom surface of the film,
   a series of apertures in the film adjacent the area coated with the adhesive,
   an absorbent pad in contact with the top surface of the film and overlying the apertures in the film,
   an adhesively coated fibrous covering overlying said absorbent pad and in contact with the top surface of the film,
   the adhesive coating of said fibrous covering terminating adjacent one edge of said covering to provide an adhesivefree edge to enable the fibrous backing to be lifted from the film,
   the fibrous covering having a surface area which is no larger than the surface area of the polymeric film.

2. The surgical dressing of claim 1 in which the polymeric film is polyurethane.

3. The surgical dressing of claim 1 in which apertures are 1 to 2 millimeters in diameter and are spaced 1 to 5 centimeters from an adjacent aperture.

4. The surgical dressing of claim 3 in which there are additional apertures in the center region of the film.

5. The surgical dressing of claim 1 in which the absorbent pad has a non-adhering facing in contact with the film.

* * * * *